United States Patent
Nagaprasad et al.

[11] Patent Number: 6,074,669
[45] Date of Patent: Jun. 13, 2000

[54] CONTROLLED DRUG DELIVERY SYSTEM FOR DILTIAZEM

[75] Inventors: Vishnubhotla Nagaprasad, Warangal; Himadri Sen, Gurgaon, both of India

[73] Assignee: Ranbaxy Laboratories Limited, New Delhi, India

[21] Appl. No.: 08/984,733

[22] Filed: Dec. 4, 1997

[30] Foreign Application Priority Data

Jan. 20, 1997 [IN] India .................. 176/DEL/97

[51] Int. Cl.[7] .................. A61K 9/26; A61K 9/52
[52] U.S. Cl. .................. 424/458; 424/469
[58] Field of Search .................. 424/456, 458

[56] References Cited

U.S. PATENT DOCUMENTS

| | | |
|---|---|---|
| 4,721,619 | 1/1988 | Panoz et al. . |
| 4,792,452 | 12/1988 | Howard et al. . |
| 4,839,177 | 6/1989 | Colombo et al. . |
| 4,880,631 | 11/1989 | Haslam et al. . |
| 4,894,240 | 1/1990 | Geoghegan et al. . |
| 4,917,899 | 4/1990 | Geoghegan et al. . |
| 4,946,686 | 8/1990 | McClelland et al. . |
| 4,968,507 | 11/1990 | Zentner et al. . |
| 4,968,508 | 11/1990 | Oren et al. . |
| 4,994,273 | 2/1991 | Zentner et al. . |
| 5,000,962 | 3/1991 | Sangekar et al. . |
| 5,002,776 | 3/1991 | Geoghegan et al. . |
| 5,169,638 | 12/1992 | Dennis et al. . |
| 5,286,497 | 2/1994 | Hendrickson et al. . |
| 5,422,123 | 6/1995 | Conte et al. . |
| 5,470,584 | 11/1995 | Hendrickson et al. . |
| 5,508,044 | 4/1996 | Buxton et al. .......... 424/495 |
| 5,529,791 | 6/1996 | Deboeck et al. . |
| 5,578,321 | 11/1996 | Sherman . |

FOREIGN PATENT DOCUMENTS

| | | |
|---|---|---|
| 2123332 | 11/1995 | Canada . |
| 0 314 206 A1 | 5/1989 | European Pat. Off. . |
| 0 373 417 A1 | 6/1990 | European Pat. Off. . |
| 0 381 181 A2 | 8/1990 | European Pat. Off. . |
| 61212517 | 9/1986 | Japan . |
| WO 96/26717 | 9/1996 | WIPO . |

*Primary Examiner*—Peter F. Kulkosky
*Attorney, Agent, or Firm*—Jayadeep R. Deshmukh

[57] ABSTRACT

A pharmaceutical composition in the form of a tablet or a capsule for the controlled release of diltiazem, comprises about 30 to about 97% by weight of a hydrophilic polymer, about 0.5 to about 30% by weight of an enteric (pH-dependent) polymer, and about 2.5 to about 60% by weight of diltiazem or a pharmaceutically acceptable salt or ester thereof. The ratio of hydrophilic polymer to enteric polymer is in the range of about 1:1 to about 15:1. Such a pharmaceutical composition releases diltiazem at a rate that allows effective plasma levels of diltiazem to be maintained over a period of twenty-four hours after administration to human adult subjects.

7 Claims, 1 Drawing Sheet

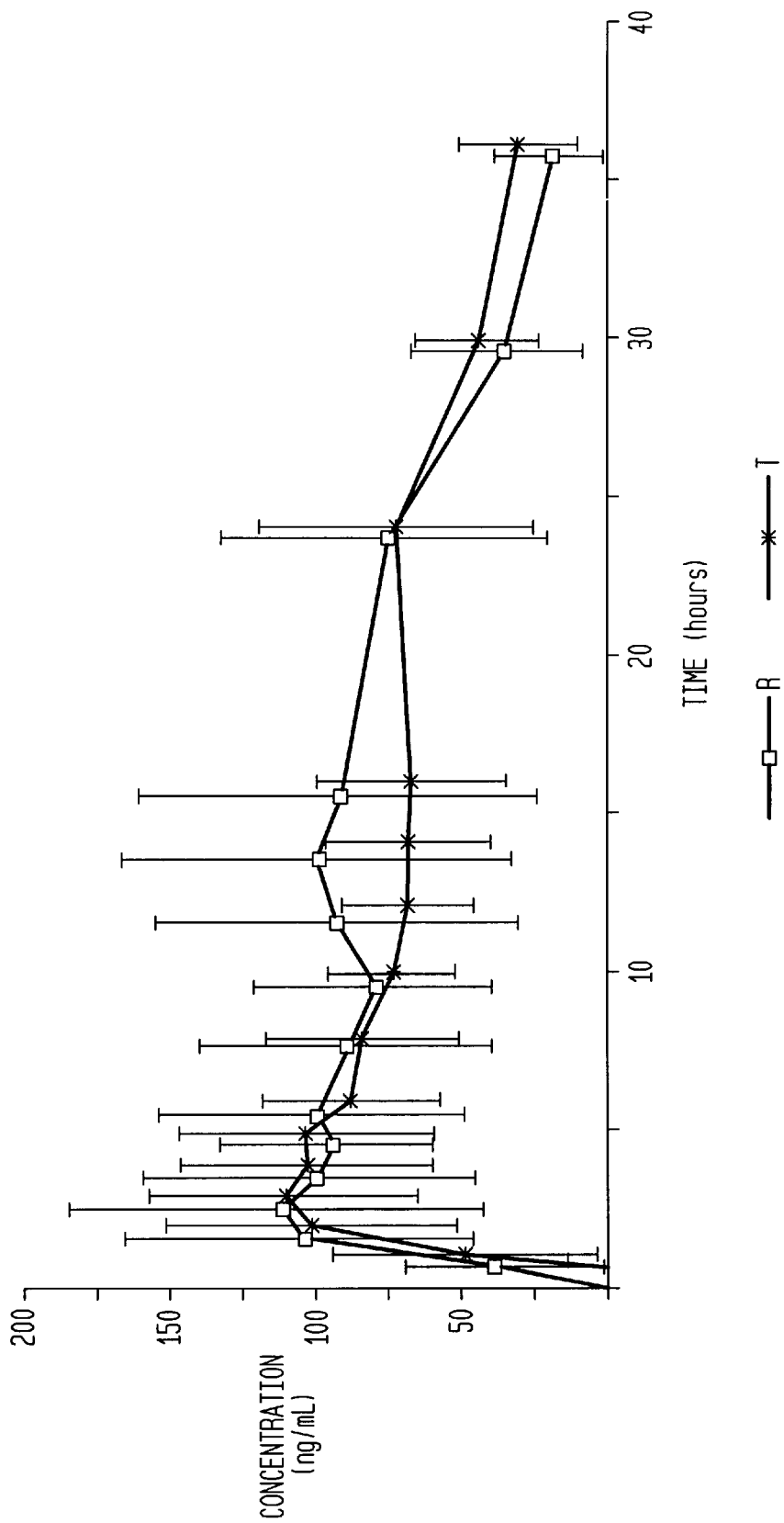

CONTROLLED DRUG DELIVERY SYSTEM FOR DILTIAZEM

FIELD OF THE INVENTION

This invention relates to a pharmaceutical composition of a controlled release drug delivery system in the form of tablets or capsules comprising one or more of a hydrophilic polymer present in amounts greater than 30% (e.g., about 30 to 97%) by weight, an enteric polymer which is present in amounts from about 0.5 to 30% by weight, and diltiazem or a pharmaceutically acceptable salt or ester thereof in amounts from about 2.5 to 60% by weight, said % by weight being based on the total weight of the composition. The ratio of hydrophilic polymer to enteric polymer is in the range of about 1:1 to 15:1, such that diltiazem is released at a rate that allows effective plasma levels of diltiazem to be maintained over a period of twenty four-hours post-administration to human subjects.

BACKGROUND OF THE INVENTION

Diltiazem hydrochloride, a benzothiazepine derivative, is a calcium channel blocker used in the treatment of angina and hypertension. The solubility of diltiazem significantly decreases as the pH increases in the gastrointestinal tract. It is required, however, that a drug delivery system deliver the drug at a constant rate as it is transported from the region of low pH in the stomach to a region of higher pH in the intestine. Such controlled delivery results in a decrease in the frequency of drug administration thereby improving patient compliance. Furthermore, controlled drug delivery systems produce constant plasma levels of active ingredients as compared to fluctuations seen when multiple doses of a conventional formulation are prescribed. Thus, controlled drug delivery systems may decrease the severity and frequency of side effects.

Several controlled drug delivery systems which are adapted for the delivery of the drug diltiazem and other drugs are known in the prior art.

U.S. Pat. No. 4,894,240 describes a controlled release diltiazem pellet formulation for once-daily oral administration consisting of a core comprising diltiazem and an organic acid, followed by a multilayer membrane surrounding the core. The membrane comprises a combination of water insoluble polymers and a minor amount of water soluble polymers. The number of layers in the membrane and the ratio of water soluble to water insoluble polymers are formulated so that diltiazem is released in a controlled manner. A formulation as described by this patent is sold in the United States under the trademark Cardizem CD™ by Hoechst-Marion-Roussel. Other patents that are related to the Cardizem CD™ pellet formulation include U.S. Pat. Nos. 5,002,776; 5,286,497; and 5,470,584. Similar pellet formulations for twice-daily oral administration are disclosed in U.S. Pat. No. 4,721,619 and are sold by Hoechst-Marion-Roussel in the United States under the trademark Cardizem SR™ by Hoechst Marion Roussel.

U.S. Pat. No. 4,917,899 discloses a controlled release diltiazem pellet formulation wherein a core of diltiazem is coated with multiple layers of water insoluble polymers. Slow release and fast release pellets are then filled into hard gelatin capsules such that the fast release pellets amount to 15% of the total blend. The formulation releases diltiazem over a 12 hour period such that it is suitable for a twice-a-day oral dosing regimen.

U.S. Pat. No. 4,839,177 discloses a controlled drug delivery system comprising a core having a defined geometry and containing a swellable and/or gellable polymeric material, and a suitable platform containing a water insoluble polymeric material applied to the core in the form of a partial coating. The intensity and duration of the swelling force and the geometry of the device are identified as factors determining the release of the active substance. Such a system is sold in the United States under the trademark Dilacor XR™ by Rhone-Poulenc Rorer. Another patent related to the Dilacor XR™ formulation is U.S. Pat. No. 5,422,123 with the difference being that the support platform described in the latter patent is an elastic support which is slowly soluble or gellable in aqueous fluids.

U.S. Pat. No. 5,529,791 discloses an extended release galenical composition comprising beads containing one or more diltiazem salts and an effective amount of a wetting agent in admixture with one or more diltiazem salts to maintain the solubility of diltiazem in each bead. The beads are coated with a microporous membrane comprising at least a water soluble or water dispersible polymer or copolymer, a water-, acid- and base-insoluble polymer, and a pharmaceutically acceptable adjuvant. A formulation as described in this patent is sold in the United States under the trademark Tiazac™ by Biovail.

U.S. Pat. No. 4,968,507 discloses an osmotic pump comprising a core containing at least one active agent and an osmotic agent surrounded by a water insoluble wall with a defined permeability to water but which is impermeable to solute, and containing at least one pH insensitive pore forming additive dispersed throughout said wall.

U.S. Pat. No. 4,880,631 discloses an osmotic pump similar to that disclosed in U.S. Pat. No. 4,968,507 (discussed below) but specifically containing diltiazem-L-malate as the active ingredient. A formulation as described by this patent is sold in the United States under the trademark Tiamate™ by Merck & Co.

European Patent App. No. 373,417 discloses a sustained release diltiazem once-daily tablet formulation with the drug dispersed in a hydrophobic matrix comprising one or more of ethylcellulose, a mixture of mono- and diglycerides, cellulose acetate, calcium phosphate, cellulose acetate butyrate and microcrystalline cellulose. Further, the document describes a water soluble coating comprising a swelling hydrophilic polymer or a barrier coating comprising a water-insoluble polymer, an enteric polymer or a mixture thereof.

European Patent App. No. 381,181 discloses a core containing diltiazem or other active agent and an osmotically active substance coated by a semi-permeable wall forming material.

U.S. Pat. No. 4,792,452 discloses a controlled release pharmaceutical formulation comprising a drug, a pH-dependent polymer which is an alginic acid salt, a pH-independent hydrocolloid gelling agent and a binder. The formulation is $Ca^{+2}$ ion free. The drug is released independent of the pH of the environment.

U.S. Pat. No. 4,946,686 describes a solubility modulated drug delivery system in which the core is comprised of a water soluble drug and a controlled release solubility modulator which is either a complexing agent or a surfactant. The core is surrounded by a water insoluble microporous wall containing pore forming additives.

U.S. Pat. No. 4,994,273 describes a solubility modulated drug delivery system in which the core is made of a water soluble drug and a solubility modulating agent comprising a complexing agent or a surfactant. The core is surrounded by a water insoluble semi-permeable wall.

U.S. Pat. No. 4,968,508 discloses a matrix tablet formulation for cefaclor, comprising from about 5% by weight to about 29% by weight of hydrophilic polymer, and from about 0.5% by weight to about 25% by weight of an acrylic polymer which dissolves at a pH in the range of between about 5.0 to about 7.4. The total weight of the polymers is less than 30% by weight of the system. The cefaclor is released within a few hours and is suitable for the administration of cefaclor twice daily.

U.S. Pat. No. 5,000,962 discloses a long acting diltiazem tablet comprising more than 35% by weight of a swellable hydrophilic polymer, a binder, a lubricant and diluent. Both coated and uncoated tablets are disclosed.

U.S. Pat. No. 5,578,321 discloses a tablet containing diltiazem hydrochloride suitable for once-daily oral administration. The tablet comprises not less than 30% by weight diltiazem hydrochloride and from 30% to 70% by weight hydroxypropyl methylcellulose having a number average molecular weight of at least 50,000.

The present invention provides a controlled drug delivery composition for once-daily administration of diltiazem to a human subject, the composition comprising diltiazem, one or more hydrophilic polymers, and an enteric polymer, wherein the ratios and amounts of enteric polymer and hydrophilic polymers are such that diltiazem is released at a constant rate over a range of pH. Enteric or pH-dependent polymers are insoluble at the acidic pH of the stomach but dissolve and/or erode in the higher pH range of about 5 to 8 encountered in the intestine. Therefore, at the lower pH in the stomach, enteric polymers impede drug release. At the higher pH in the intestine, the enteric polymers dissolve and/or erode. Thus, in spite of the higher solubility of the drug in acidic fluids, it is released at more or less the same rate throughout the pH range likely to be encountered in the gastrointestinal tract.

In addition to the use of a combination of defined ratios of hydrophilic and enteric polymers, the use of a high quantity of polymers in the present invention contributes towards ensuring a constant rate of release of the drug and therefore a uniform and consistent absorption. Effective plasma levels are maintained for a period as long as 24 hrs and persist near the minimum effective level for up to 30 hrs. This further ensures uniform blood level profiles and eliminates the risk of overdose. Such an elimination of risk of overdose is of particular concern in once-daily formulations as they contain a quantity of active medicament which is several times the conventional dose of the medicament.

The release of a drug from a matrix system is dependent on the physiochemical nature of the drug, and the present invention provides a composition comprising hydrophilic and enteric polymers in ratios and amounts that results in controlled release of diltiazem at a rate that benefits therapy with diltiazem.

The present invention is easy to produce. Prior art processes are either more time consuming or expensive. For example, the process for making the coated pellets in capsules such as Cardizem CD™ that are described in U.S. Pat. No. 4,894,240, and the drug delivery system of Dilacor XR™ described in U.S. Pat. No. 4,839,177, are complex and expensive to make.

BRIEF DESCRIPTION OF THE DRAWING

FIG. 1 shows a linear plot of mean serum diltiazem concentration versus time in healthy male human subjects who have been administered the pharmaceutical composition of the present invention and a reference diltiazem product (Dilacor XR™).

SUMMARY OF THE INVENTION

This invention is directed to a controlled release pharmaceutical composition in the form of tablets or capsules comprising about 30 to about 97% by weight of one or more hydrophilic polymers, about 0.5 to about 30% by weight of an enteric polymer, and about 2.5 to about 60% by weight of diltiazem or a pharmaceutically acceptable salt or ester thereof The ratio of hydrophilic polymer to enteric polymer is from about 1:1 to about 15:1. This formulation allows the diltiazem to be released at a rate such that effective plasma levels of diltiazem are maintained over a period of twenty-four hours after administration to human subjects.

DETAILED DESCRIPTION OF THE INVENTION

The present invention is directed to a matrix of well mixed components comprising diltiazem or its pharmaceutically acceptable salt or ester, one or more hydrophilic polymers, an enteric polymer and pharmaceutically acceptable excipients. The pharmaceutical composition is either compressed into tablets or granulated and filled into capsules.

Suitable hydrophilic polymers include cellulose ethers such as hydroxypropyl methylcellulose, hydroxypropylcellulose, or other water soluble or swellable polymers such as sodium carboxymethyl cellulose, xanthan gum, acacia, tragacanth gum, guar gum, karaya gum, alginates, gelatin, albumin and the like. These hydrophilic polymers also include polyacrylate polymers, such as homopolymers based on acrylic acid cross-linked with allyl sucrose or allyl pentaerythritol, or copolymers based on acrylic acid and long chain ($C_{10}$–$C_{30}$) allyl acrylates cross-linked with allylpentaerythritol. The polyacrylate polymers may be used alone or in admixture with cellulose ethers such as methylcellulose, hydroxypropyl methylcellulose, hydroxypropylcellulose, hydroxyethylcellulose, and the like. According to the invention, the hydrophilic polymers are present in amounts ranging from about 30% to about 70% by weight of the system.

The preferred hydrophilic polymers are selected from the group consisting of cellulose ethers such as hydroxypropyl methylcellulose, hydroxypropylcellulose, methylcellulose and mixtures thereof.

According to a preferred embodiment of the present invention, the hydrophilic polymer is a mixture of a hydroxypropyl methylcellulose whose 2% by weight aqueous solution has a viscosity greater than 10,000 cPs, and hydroxypropylcellulose whose 2% by weight aqueous solution has a viscosity less than 5000 cPs. The hydroxypropyl methylcellulose may be present in amounts from about 10% to 70% by weight, preferably from about 20% to 30% by weight, of the total weight of the system. The hydroxypropylcellulose may be present in amounts from about 5% to 50% by weight, preferably from about 15% to 25% by weight, of the system.

Examples of hydroxypropyl methylcellulose polymers that may be used in the present invention include those available from Dow Chemical Co. under the brand name Methocel, such as, Methocel K15M, Methocel K100M, and the like. Hydroxypropylcellulose polymers that may be used in the present invention include, for example, those available under the brand name Klucel™ from Aqualon and HPC™ available from Nippon Soda Co., such as HPC-L™, HPC-M™, Klucel GF™, Klucel JF™, Klucel HF™ and the like.

The enteric polymers that may be used in the present invention include polyacrylate copolymers such as Methacrylic Acid Copolymer, USP/NF, Types A, B or C, which are available from Rohm GmbH under the brand name Eudragit™; cellulose derivatives, such as cellulose acetate phthalate, hydroxypropyl methylcellulose phthalate, hydroxypropyl methylcellulose acetate succinate; and polyvinyl acetate phthalate and the like.

In a preferred embodiment of this invention, the enteric polymer is a polyacrylate enteric polymer. The enteric polymer is present in amounts from about 0.5% to 30% by weight of the system. In a further preferred embodiment of the invention, the enteric polymer is present in amounts from about 0.5% to 10% by weight of the system.

According to another preferred embodiment of the invention, the total weight of the hydrophilic polymers and enteric polymers is in the range of about 35% to 97.5% by weight of the system.

The present invention may also contain pharmaceutically acceptable excipients such as diluents, binders, lubricants, buffering agents, preservatives, stabilizers, surfactants, colorants and the like. The system may be formed into tablets, as dosage form, by conventional means, or into granules or cohesive slugs by conventional means, and the granules or slugs thus prepared may be filled into capsules. Optionally, the tablets may be coated or one or more tablets may be filled into one capsule in order to improve the pharmaceutical quality attributes such as taste and appearance.

A preferred method of preparing the composition of this invention comprises sifting the drug, polymers and diluents; followed by mixing them with about one-half of the lubricants. The well mixed mass is then compacted into slugs and then granulated by screening. The granules are lubricated with the second half of the lubricants and then compressed into tablets. The tablets are then filled into capsules.

The invention is further illustrated by the following examples:

EXAMPLE 1

This example illustrates the process of making the pharmaceutical composition of the invention in the form of compressed tablets.

TABLE 1

(Formulation 1)

| INGREDIENTS | mg/tablet (% w/w) |
|---|---|
| Diltiazem Hydrochloride | 240 (40.7) |
| Eudragit L-100-55 | 20 (3.4) |
| Methocel K100M | 175 (29.7) |
| Hydroxypropyldcellulose (HPC-M) | 100 (17.0) |
| Lactose | 35 (5.9) |
| Magnesium Stearate | 6 (1.0) |
| Talc | 8 (1.4) |
| Aerosil-200 (Colloidal silicon Dioxide) | 6 (1.0) |
| Total | 590 (100.0) |

Diltiazem hydrochloride, Eudragit L-100, Methocel K-100-M, hydroxypropylcellulose-M and lactose in the amounts shown in Table 1 were screened through a No. 60 mesh (British Standard Sieve ("BSS");250 $\mu$m). The screened mass along with half the quantities of magnesium stearate, talc and Aerosil-200 were mixed together for 15 minutes. The well mixed components were compressed into slugs using a 16 station tablet press. The slugs were sized through a No. 22 mesh (BSS;710 $\mu$m). The resulting granules were lubricated with the remaining half of magnesium stearate, talc and Aerosil and then compressed into capsule-shaped tablets using standard concave punches and 15.2×6.7 mm dies on a 16-station tablet press.

The release of diltiazem from these tablets was evaluated using USP Type II apparatus in a dissolution medium consisting of 0.1N HCl in one test, and a pH 6.8 phosphate buffer in the second test. The paddle speed was 100 rpm. The results are given in Table 2.

TABLE 2

| | PERCENT RELEASE* | |
|---|---|---|
| TIME (HRS.) | 0.1N HCl | pH 6.8 Buffer |
| 2 | 19.1 (6.5) | 14.9 (6.0) |
| 4 | 30.8 (6.8) | 25.7 (5.4) |
| 8 | 49.6 (6.0) | 41.6 (6.0) |
| 12 | 64.5 (4.8) | 53.3 (5.9) |
| 14 | 70.9 (4.1) | 57.8 (6.0) |

*Figures in parenthesis indicate percent coefficient of variation.

The low percent coefficient of variation indicates uniformity and reproducibility of release of diltiazem from the tablets. The results also indicate that the rate of release of diltiazem from the drug delivery system was not appreciably affected by the pH of the dissolution medium.

EXAMPLE 2

This example illustrates the process of making the pharmaceutical composition of the invention in the form of multiple tablets filled into capsules.

TABLE 3

(Formulation 2)

| Ingredients | mg/capsule (% w/w) |
|---|---|
| Diltiazem Hydrochloride | 240 (33.3) |
| Eudragit L-100 | 65 (9.0) |
| Methocel K-100-M | 175 (24.3) |
| Hydroxypropylcellulose (HPC-M) | 125 (17.4) |
| Lactose | 100 (13.9) |
| Magnesium Stearate | 7 (1.0) |
| Aerosil | 8 (1.1) |
| Total | 720 (100.0) |

The granules were prepared from the ingredients in the amounts shown in Table 3 in the same manner as in Example 1 and then compressed into 180 mg tablets using flat bevelled 7.0 mm punches and dies on a 16 station tablet press. Four such tablets were filled into each Ad of size '00' capsules.

The release of diltiazem from these capsules was evaluated as described in Example 1, and the results are given in Table 4.

TABLE 4

| | Percent Release* | |
|---|---|---|
| Time (Hrs.) | 0.1N HCl | pH 6.8 Buffer |
| 2 | 31.9 (1.3) | 26.87 (4.0) |
| 4 | 50.7 (0.5) | 44.2 (3.4) |
| 8 | 77.5 (0.5) | 74.3 (6.9) |
| 12 | 93.1 (0.8) | 87.47 (5.7) |
| 15 | 97.0 (3.6) | 96.77 (3.7) |

*Figures in parenthesis indicate coefficient of variation.

The low percent coefficient of variation indicates uniformity and reproducibility of release of diltiazem from the capsules. The results also indicate that the rate of release of diltiazem from the drug delivery system was not appreciably affected by the pH of the dissolution medium.

EXAMPLE 3

This example illustrates the process of making the pharmaceutical composition of the invention in the form of tablets filled into capsules.

TABLE 5

(Formulation 3)

| Ingredients | mg/capsule (% w/w) |
|---|---|
| Diltiazem Hydrochloride | 240 (40.0) |
| Eudragit L-100-55 | 60 (10.0) |
| Methocel K-100-M | 135 (22.5) |
| Hydroxypropylcellulose (HPC-M) | 125 (20.8) |
| Lactose | 20 (3.3) |
| Magnesium Stearate | 6 (1.0) |
| Talc | 8 (1.3) |
| Aerosil | 6 (1.0) |
| Total | 600 (100.0) |

Granules were prepared from the ingredients shown in Table 5 in the same manner as described in Example 1 except that for granulation of the powder mass in this example, roll compaction replaced slugging on a tablet press. The granules were compressed into tablets using 19.0×6.2 mm capsule shaped punches. Each tablet was filled into a single size '0' capsule.

The release of diltiazem from these capsules was evaluated as described in Example 1, and the results are given in Table 6.

TABLE 6

| Time (Hrs.) | Percent Release* 0.1N HCl | pH 6.8 Buffer |
|---|---|---|
| 2 | 21.63 (6.4) | 15.83 (1.0) |
| 4 | 33.87 (6.7) | 27.03 (0.6) |
| 8 | 52.87.(5.8) | 46.70 (0.7) |
| 12 | 68.0 (4.0) | 62.63 (0.75) |
| 18 | 85.1 (1.76) | 78.33 (1.5) |

*Figures in parenthesis indicate percent coefficient of variation.

The low percent coefficient of variation indicates uniformity and reproducibility of release of diltiazem from the capsules. The results also indicate that the rate of release of diltiazem from the drug delivery system was not appreciably affected by the pH of the dissolution medium.

For each of the formulations of Examples 1 to 3, at least six tablets were tested for dissolution. Overall, more than two hundred tablets were made in accordance with the present invention and were tested for dissolution. The physical integrity of the mix was maintained throughout the period of dissolution, demonstrating that none of the units showed physical failure. This is attributable to the use of more than 30% by weight of hydrophilic swelling polymer and less than 30% by weight of the enteric polymer in the system. Thus, there was low variability in rate of release and risks of dose dumping are virtually eliminated.

A formulation in the form of a single tablet in a capsule prepared according to the present invention was evaluated in-vivo in 6 young healthy male volunteers in comparison to a reference product (Dilacor XR:™ 240 mg capsule). The test and reference formulations were administered as a single 240 mg dose. Concentrations of diltiazem in serum up to a period of 36 hrs post-administration were measured. The serum concentration vs time profile for the reference (R) and the test (T) products are given in FIG. 1. Controlled release formulations, in certain instances, may give a slow onset of action. However, it is evident from FIG. 1 that the diltiazem formulation prepared according to the present invention gives effective absorption within a short period such that minimum effective plasma levels (50 ng/ml) are achieved within 2 hrs. Peak plasma levels are achieved in about 5 hours. Furthermore, it is evident that effective levels between 50 ng/ml to 200 ng/ml are maintained up to 24 hrs. and persist near the minimum effective level for up to 30 hrs.

While the invention has been described by reference to specific examples, this was for purposes of illustration. Numerous alternatives will be apparent to those skilled in the art and are considered to be within the scope of the invention.

What is claimed is:

1. A once-a-day controlled release pharmaceutical composition in the form of a matrix of well-mixed components, comprising: (a) about 30 to about 90% by weight of a hydrophilic polymer, (b) about 0.5 to about 30% by weight of a pH dependent enteric polymer, and (c) about 2.5 to about 60% by weight of diltiazem or a pharmaceutically acceptable salt or ester thereof, wherein the hydrophilic polymer to enteric polymer is in the range of about 1:1 to about 15:1, wherein the hydrophilic polymer and the enteric polymer comprise about 35 to about 97.5% by weight of said composition, and wherein the hydrophilic polymer comprises a mixture of about 10% to about 70% by weight of hydroxypropyl methylcellulose and about 5% to about 50% by weight of hydroxypropylcellulose, of said composition.

2. A once-a-day controlled release pharmaceutical composition in the form of a matrix of well-mixed components, comprising: (a) about 30 to 90% by weight of a hydrophilic polymer, (b) about 0.5 to about 30% by weight of a pH-dependent enteric polymer, and (c) about 2.5 to about 60% by weight of diltiazem or a pharmaceutically acceptable salt or ester thereof, wherein the ratio of hydrophilic polymer to enteric polymer is in the range of about 1:1 to about 15:1, wherein the hydrophilic polymer and the enteric polymer comprise about 35 to about 97.5% by weight of said composition and wherein the hydrophilic polymer comprises a mixture of about 20% to about 30% by weight of hydroxypropyl methylcellulose and about 15% to about 25% by weight of hydroxypropylcellulose, of said composition.

3. The pharmaceutical composition of claim 1, wherein the hydrophilic polymer comprises a mixture of a hydroxypropyl methylcellulose whose 2% by weight aqueous solution has a viscosity greater than 10,000 cPs, and a hydroxypropylcellulose whose 2% by weight aqueous solution has a viscosity less than 5000 cPs.

4. The pharmaceutical composition of claim 3, wherein the enteric polymer is a polyacrylate polymer.

5. The pharmaceutical composition of claim 3, wherein the enteric polymer comprises about 0.5 to about 10% by weight of the composition.

6. The pharmaceutical composition of claim 3 in the form of a tablet.

7. The pharmaceutical composition of claim 3 in the form of at least one tablet filled into a capsule.

* * * * *